United States Patent [19]

Munsch et al.

[11] Patent Number: 4,794,926
[45] Date of Patent: Jan. 3, 1989

[54] LANCET CARTRIDGE

[75] Inventors: John M. Munsch, Libertyville; Mark D. Ruby, Lake Zurich; William J. Schnell, Libertyville; Jimmy L. Miller, Waukegan, all of Ill.

[73] Assignee: Invictus, Inc., Libertyville, Ill.

[21] Appl. No.: 933,843

[22] Filed: Nov. 24, 1986

[51] Int. Cl.[4] .............................................. A61B 17/32
[52] U.S. Cl. ..................................................... 128/314
[58] Field of Search .................... 128/314, 315, 329 R, 128/770; 604/46

[56] References Cited

U.S. PATENT DOCUMENTS

| 2,801,633 | 2/1954 | Ehrlich | 128/314 |
| 3,030,959 | 4/1962 | Grunert | 128/314 |
| 3,760,809 | 9/1973 | Campbell | 128/329 X |
| 4,539,988 | 9/1985 | Shirley et al. | 128/329 R X |
| 4,715,374 | 12/1987 | Maggio | 128/314 |

FOREIGN PATENT DOCUMENTS

| 2131297 | 1/1973 | Fed. Rep. of Germany | 128/314 |
| 2461273 | 9/1976 | Fed. Rep. of Germany | 128/315 |
| 289191 | 11/1953 | Switzerland | 128/315 |
| 1080986 | 9/1965 | United Kingdom | 128/315 |

Primary Examiner—Michael H. Thaler

[57] ABSTRACT

Described is a lancet cartridge for drawing blood samples from the finger of a patient which includes a first housing for receiving a lancet disk having a plurality of radially extending lancets, each lancet having a tooth projecting from the end thereof, and a second housing engageable with the first housing, the housings being rotatable with respect to each other, the one housing includes a ramp for receiving the end of the lancets whereby the lancet is elevated when the cartridge housing is rotated. A platform is positioned in one of the housings to receive the lancet as it is elevated by the ramp to thereby place the lancet in a cocked position. The second housing member includes at least one opening through which the end of the lancets can project to pierce the patient's finger. A trigger is positioned to be activated when a finger is placed in the opening to release the cocked lancet from the platform and pierce the patient's finger. As the housing is rotated the lancets are successively positioned on the platform so that the lancet device can be used to take multiple blood samples. If desired, the device can be disposable.

12 Claims, 3 Drawing Sheets

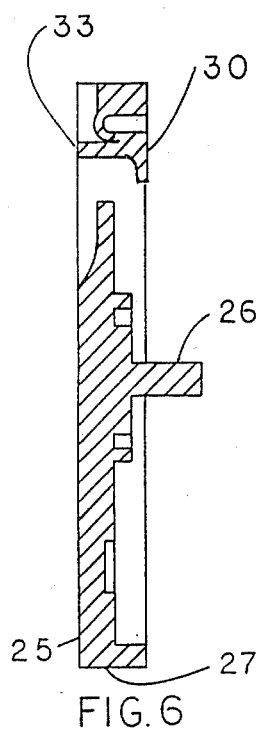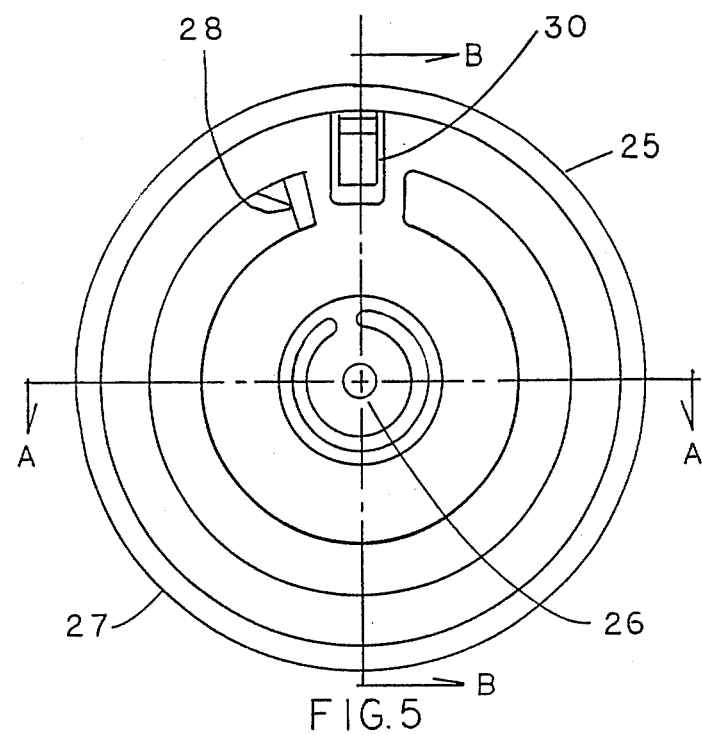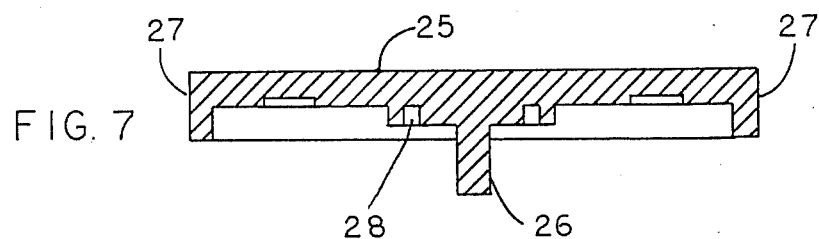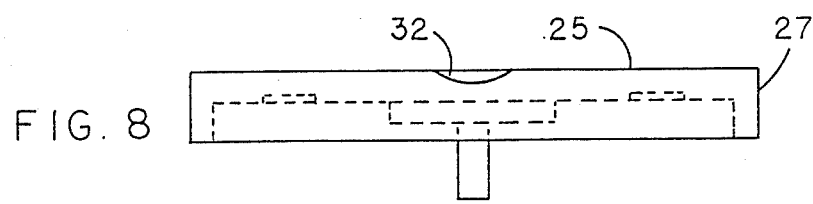

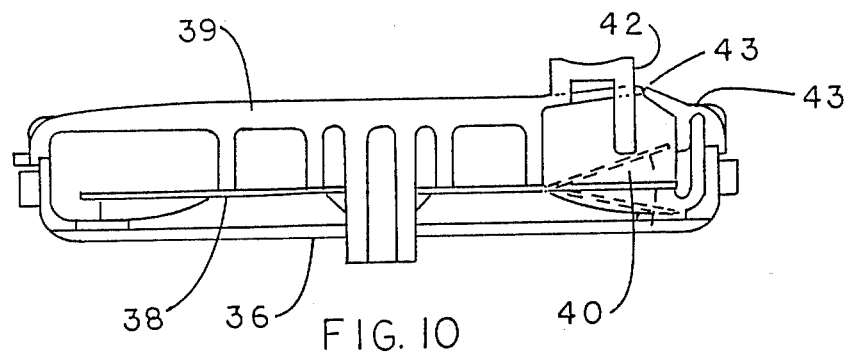
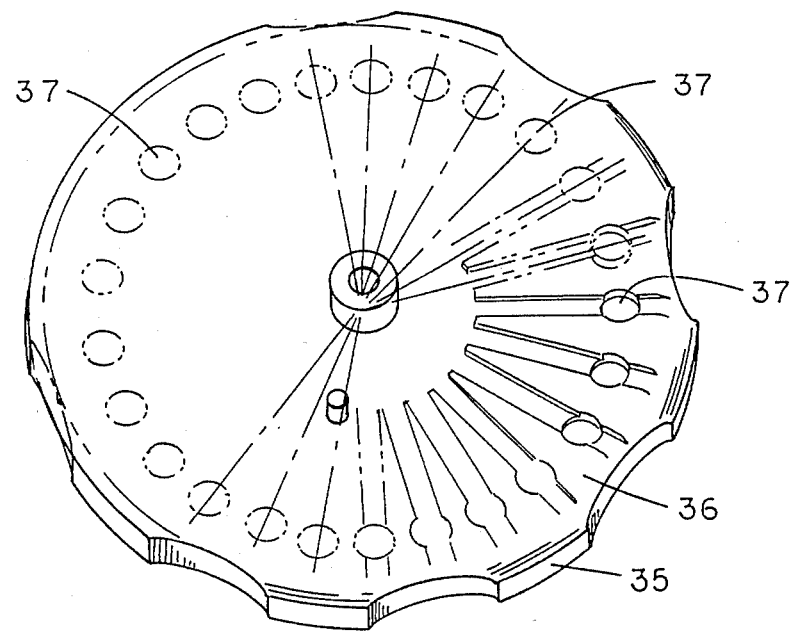

LANCET CARTRIDGE

BACKGROUND OF THE INVENTION

For the effective management of diabetes it is often recommended by physicians that the patient test his own blood glucose levels. Blood is generally drawn from the finger tips and most patients find that blood sampling is facilitated by automatic lancet devices. Most automatic blood sampling devices currently available require the loading and unloading of a single lancet for each blood sampling. A blood sampling device with multiple lancets would therefore be desirable.

SUMMARY OF THE INVENTION

The invention comprises a lancet cartridge which includes a disk with a series of radial arms each having a tooth at the end. The disk is retained between a first housing and a second housing member, the two housing members being engageable rotatable with respect to each other. As the housing members are rotated with respect to each other, the disk is likewise rotated, or alternatively, a trigger mechanism in the housing is rotated, and an arm or lancet is elevated by a ramp. As the lancet disk or housing is rotated, a first lancet sits on the platform which is likewise positioned in the housing member to thereby cock the lancet. A finger is then placed in an opening adjacent to a trigger which is adapted to release the cocked lancet from the platform. As the trigger is depressed, the lancet will slip off the platform, acting as its own spring, and will puncture the finger. The next time a blood sample is to be taken, the procedure is repeated using the next radial arm as the lancet. Thus, the cartridge can be used repeatedly until all of the lances have been used.

BRIEF DESCRIPTION OF DRAWINGS

The invention will be described in conjunction with the following drawings in which:

FIG. 5 is a top view of a second housing member which includes a ramp, platform and trigger for receiving the radially extending lancets;

FIG. 6 is a side elevational view in cross-section as seen along the line B—B of FIG. 5;

FIG. 7 is a cross-sectional view of the housing member of FIG. 5 as seen along the line A—A;

FIG. 8 is a cross-sectional view illustrating the opening in the housing member of FIG. 5 together with the trigger for releasing the lancet;

FIG. 9 is an isometric view of an alternative embodiment of the invention in which one of the housing members includes a plurality of openings for projection of the lancet; and FIG. 10 is a cross-sectional view of the embodiment of FIG. 9 illustrating the lancet disk and trigger means.

DETAILED DESCRIPTION OF THE INVENTION

Figure 3:
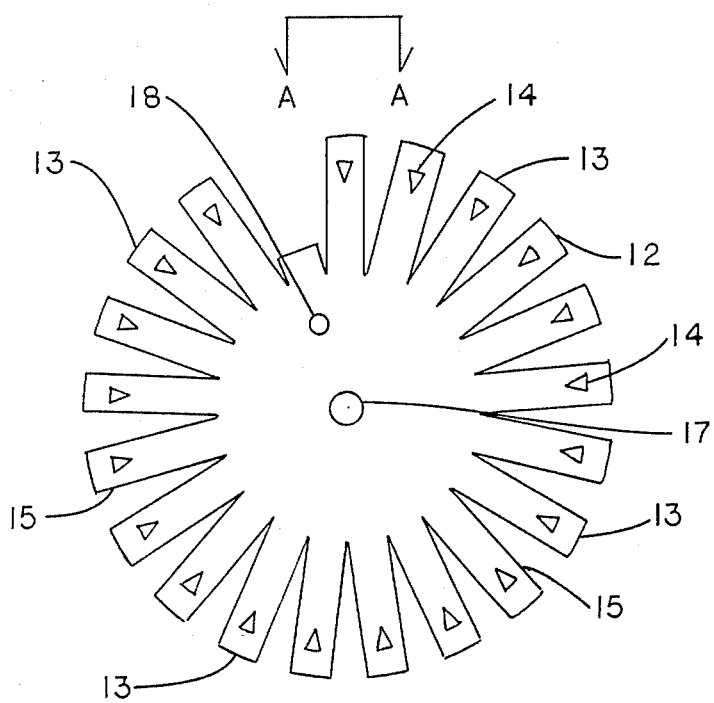
FIG. 3 is a top view of a lancet disk of the invention.
Figure 4:
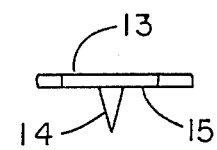
FIG. 4 is an end view as seen along the line A—A of FIG. 3 illustrating the end of a lancet projecting tooth for piercing a finger.
Figure 1:
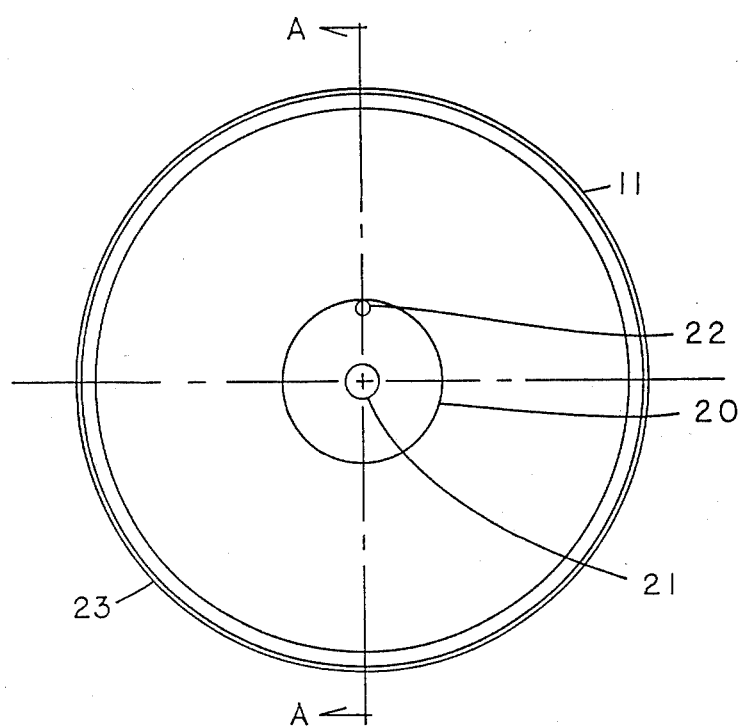
FIG. 1 is a top plan view of a first housing member for receiving a lancet disk.
Figure 2:
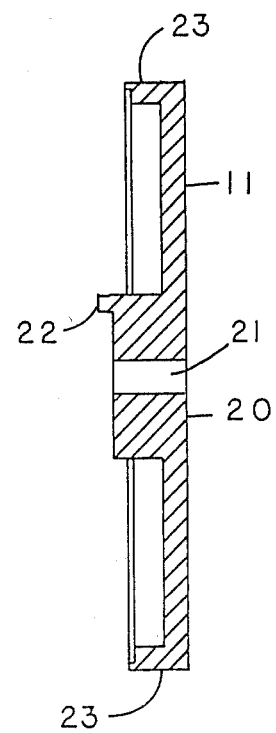
FIG. 2 is a side elevational view of the first housing of FIG. 1 as seen along the line A—A.

One embodiment of the blood sampling device or lancet cartridge of the present invention is illustrated in the drawings in which FIG. 1 illustrates a first housing member 11 for rotating and receiving the lancet disk 12, illustrated in FIG. 3. The lancet disk 12 includes a plurality of radially extending lancets 13, each having a tooth 14 projecting from the end 15 of the lancet as best illustrated in FIG. 4. The lancet disk 12 includes a central opening 17 and a second opening 18 for receiving a pin 22 in the housing 11 as hereinafter described.

The first housing member 11 includes a core 20 having an axial opening 21 for engagement with the second housing member 25 hereinafter described and a pin projecting from the core which is received in the opening 18 in the lancet disk 12, groove 28 and sidewalls 23.

The second housing member 25 illustrated in FIGS. 5–8 for retaining the lancet disk 12 includes an axially extending pin 26 which is engageable with the axial opening 21 of the first housing member 11 whereby the two housing members are engageable to retain the lancet disk 12 and are rotatable with respect to each other. The second housing member 25 includes sidewalls 27 and has a ramp 29 positioned therein for elevating each extending lancet 13 as the housing members are rotated with respect to each other and a platform 30 positioned therein for receiving each lancet 13. The second housing member 25 also includes an opening 32 for receiving the patient's finger. A trigger 33 is positioned to be activated by the patient's finger when the finger is placed in the opening to thereby release the cocked lancet 13 which is positioned on the platform 30.

In use, as the first housing member 11 is rotated with respect to the second housing member 25, the lancet disk 12 retained within the first housing member 11 and maintained in position by the projecting pin 22 is likewise rotated. As the lancet disk 12 is rotated, a radially extending lancet 13 will engage the ramp 29 which will elevate the lancet and seat it on the platform 30 where the lancet 13 will be in a cocked position. As a finger is placed in the opening 32 in the second housing member 25, the trigger 33 will be depressed by the finger which will cause the lancet 13 to slip off the platform 30 and, acting as its own spring, cause the tooth 14 of the lancet 13 to pierce the finger and, thus, produce a blood sample. The next time a blood sample is to be taken, the procedure is repeated using the next radially extending lancet 13 on the lancet disk 12. Thus, as the housing members 11, 25 are rotated with respect to each other, the device will successively position a lancet 13 on the platform 30 so that the lancet cartridge can be used repeatedly until all of the lancets have been used. As illustrated, the lancet disk 12 includes twenty radially extending lancets 13.

An alternative embodiment 35 is illustrated in FIGS. 9 and 10 in which one housing member 36 includes a plurality of openings 37 for receiving the patient's finger. In this embodiment, the lancet disk 38 is stationary and the first housing member 39 is rotated with respect to the second housing member 36. A ramp or plough-shaped member 40 is positioned in the housing member 39 and elevates the individual lancet as first housing member 39 is rotated and positions it on a platform as described with respect to the embodiment of FIGS. 1–8. As illustrated, the trigger 42 includes weakened portions or hinges 43 so that as the trigger 42 is depressed, the hinges 43 will allow the trigger 42 to disengage the lancet and cause it to slip off the platform and pierce the patient's finger. A thin, plastic sterility seal (not shown) seals each opening 37 and protects each lancet tooth. In use, the patient places a finger over an opening 37 and presses the trigger 42 on the opposite side to release the lancet. As illustrated, the housing member 36 includes a plurality of openings 37 so that the patient can use each opening 37 successively until all of the lancets are used.

What is claimed is:

1. A lancet cartridge for drawing blood samples from the finger of a patient comprising a first housing member carrying a lancet disk having a plurality of radially extending lancets defining free, flexible lancet ends, each lancet having a tooth projecting from the free end thereof in a transverse direction to the axis of said lancet;

a second housing member engageable with the first housing member and rotatable therewith, said second housing member including a ramp for receiving the ends of the lancets whereby each lancet may be elevated as the first housing member is rotated, and a platform positioned in said second housing member to receive each lancet as it is elevated by the ramp to place the lancet in a cocked position, the second housing member having an opening therein through which the end of the lancet having a tooth thereon can project, said opening being suitable for receiving the finger of a patient, and trigger means for releasing the cocked lancet from the platform, said trigger means being activated when the patient's finger is placed in the opening in the housing to release the cocked lancet which acts as its own spring to thereby pierce the finger of the patient, the first and second housing members being rotatable with respect to each other to rotate the lancet disk and successively position a lancet on the platform.

2. The lancet cartridge of claim 1 wherein the lancet disk is fixed in the first housing member whereby when the housing members are rotated with respect to each other, the lancet disk will rotate to successively position a lancet on the platform positioned below the opening.

3. The lancet cartridge of claim 2 wherein the trigger means is positioned in the opening in the housing and arranged to be activated by the patient's finger when the finger is placed in the opening.

4. The lancet cartridge of claim 1 wherein the second housing member includes a plurality of openings for receiving a patient's finger and wherein the lancet disk is retained in a first housing member, the first housing member being rotatable with respect to the second housing member whereby the trigger is successively rotated under a different lancet thereby lifting the lancet to a cocked position.

5. The lancet cartridge of claim 4 wherein the trigger means comprises a trigger portion and a hinged portion whereby the trigger can be depressed to release the lancet from the platform and pierce the patient's finger.

6. The lancet cartridge of claim 4 including a sterility seal covering each opening and the point of the lancet.

7. A lancet cartridge for drawing blood samples from the finger of a patient comprising a first housing member for receiving a lancet disk defining a plurality of radially extending lancets, each lancet defining a free, flexible end, said end defining a tooth projecting in transverse relation to the axis of said lancet, said lancet disk being carried with said first housing member in rotationally immovable relation;

a second housing member engaging said first housing member and enclosing said lancet disk, said second housing member being rotatable relative to said first housing member and lancet disk, said second housing member defining aperture means positioned to permit the free end and tooth of at least one lancet to pass into said aperture means by flex motion, means for retaining said lancet in a position spaced from said aperture within said first and second housing members, and means for releasing said lancet from said position to cause it to drive forward, acting as its own spring, into said aperture, whereby blood may be drawn from a patient having a finger positioned at said aperture.

8. The lancet cartridge of claim 7 in which the second housing member includes a plurality of openings, said openings being respectively positioned to permit free ends and attached teeth of the respective lancets to enter therein, whereby said lancet cartridge may be used for drawing multiple blood samples without reusing an individual lancet.

9. A lancet cartridge for drawing blood samples from the finger of the patient comprising first and second housing members in rotatable relation with each other and enclosing a lancet cartridge comprising a lancet disc having a plurality of radially extending lancets, each lancet having a free, flexible end, and a tooth projecting from said end in a direction transverse to the axis of said lancet; the lancet disc being in rotatably fixed relation with said first housing member, said second housing member defining a ramp for receiving the free ends of said lancets, said housing member also defining a platform to receive and cock the free ends of said lancets, said ramp functioning to sequentially elevate said lancets into engagement with said platform as the second housing member is rotated relative to the first housing member, to place each lancet sequentially into a cocked position; trigger means for releasing the cocked lancet from said platform, whereby, one said lancet is released from engagement with said platform by said trigger means, the lancet acting as its own spring to snap said free end and tooth into the opening, whereby said tooth can pierce a patient's finger placed at said opening.

10. The lancet cartridge of claim 9 in which the trigger means is positioned in the opening in the housing and arranged to be activated by the patient's finger when the finger is placed in the opening.

11. The lancet cartridge of claim 9 in which said second housing member includes a plurality of openings through which the individual lancets sequentially snap.

12. The lancet cartridge of claim 9 including a sterility seal covering said opening and the point of said lancet.

* * * * *